(12) United States Patent
Vogelstein et al.

(10) Patent No.: US 6,177,251 B1
(45) Date of Patent: Jan. 23, 2001

(54) METHOD FOR DETECTION OF TARGET NUCLEIC ACID BY ANALYSIS OF STOOL

(75) Inventors: Bert Vogelstein; Kenneth W. Kinzler, both of Baltimore, MD (US)

(73) Assignee: The Johns Hopkins University, Baltimore, MD (US)

( * ) Notice: Under 35 U.S.C. 154(b), the term of this patent shall be extended for 0 days.

(21) Appl. No.: 09/328,114

(22) Filed: Jun. 8, 1999

Related U.S. Application Data

(62) Division of application No. 08/297,265, filed on Aug. 26, 1994, now Pat. No. 5,910,407, which is a continuation of application No. 07/861,910, filed on Apr. 1, 1992, now abandoned.

(51) Int. Cl.[7] ............................. C12Q 1/68; C12P 19/34; C07H 21/00
(52) U.S. Cl. ......................... 435/6; 435/91.2; 536/25.4; 536/25.41; 536/25.42
(58) Field of Search .................... 435/6, 91.2; 536/25.4, 536/25.41, 25.42

(56) References Cited

U.S. PATENT DOCUMENTS

| | | |
|---|---|---|
| 4,358,535 | 11/1982 | Falkow et al. . |
| 4,800,159 | 1/1989 | Mullis et al. . |
| 4,935,342 | 6/1990 | Seligson et al. . |
| 4,992,364 | 2/1991 | Sansonetti et al. . |
| 5,024,934 | 6/1991 | Lee . |
| 5,037,959 | * 8/1991 | Clarke et al. ......................... 530/370 |
| 5,053,331 | * 10/1991 | Clarke et al. ..................... 435/172.3 |
| 5,330,892 | 7/1994 | Vogelstein et al. . |
| 5,352,775 | 10/1994 | Albertsen et al. . |
| 5,482,834 | * 1/1996 | Gillespie ................................. 435/6 |
| 5,612,473 | * 3/1997 | Wu et al. ........................ 536/25.42 |
| 5,670,325 | * 9/1997 | Lapidus et al. ........................... 435/6 |

FOREIGN PATENT DOCUMENTS

| | | |
|---|---|---|
| 9111534 | 1/1991 | (WO) . |

OTHER PUBLICATIONS

Ma et al., Detection of P53 Gene Mutations in Epoliated Human Colonic Epithelial Cells Isolated from Stools of Subjects Undergoing Colomsocopy, *Gast. Onc.*, 104(4):A–423 (1993).

Nollau et al., "Detection of K–ras Mutations in Stools of Patients with Colorectal Cancer by Mutant–Enriched PCR", *Int. Jour. Cancer*, 66:332–336 (1996).

Nakamura, et al., "Mutations of the addenomatous polyposis coli gene in familial polyposis coli patients and sporadic colorectal tumors", Princess Takamatsu Symp 22, pp 285–292: Abstract Only (1991).

Robert A. Weinbert; Tumor Suppressor Genes; Science, vol. 254 1138–1146.

Ellen Solomon, et al.; Chromosome Aberrations and Cancer; Articles 1153–1160, Nov. 22, 1991.

Monica Hollstein, et al.; p53 Mutations in Human Cancers: Articles pp 46–53; Jul. 5, 1991.

Sidransky et al.; Science 256; 102–105 (1992).

Allard et al.; J. Clinical Microbiol. 28: 2689–2667 (1990).

Coll et al.; J. Clinical Microbiol. 27: 2245–2248 (1989).

Manistis et al.; Molecular Cloning a Laboratory Manuel, Cold Spring Harbor Laboratory, 1982, Goelz et al.; Bioch Bioph. Reg. Comm. 130(1): 118–126, 1985.

Durrant et al., "Identification of Mutant P53 in the Stool of Patients with Colorectoral Cancer," *Br. Jour. Cancer*, 67:20, (1993).

\* cited by examiner

*Primary Examiner*—Kenneth R. Horlick
(74) *Attorney, Agent, or Firm*—Banner & Witcoff, Ltd.

(57) ABSTRACT

A stool lysis buffer having a high concentration of buffer, a chelating agent, and a salt has the ability to lyse mammalian cells but not bacterial cells. Lysed cells release nucleic acids into the buffer. A particulate fraction is removed which includes the unlysed bacterial cells.

26 Claims, 1 Drawing Sheet

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: misc_RNA
      (B) LOCATION: 1..28

(xi) SEQUENCE DESCRIPTION: SEQ ID NO:1:

TCCTTAAGTA CTGACTTATA TTTGAACA      28

(2) INFORMATION FOR SEQ ID NO:2:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: misc_RNA
      (B) LOCATION: 1..30

(xi) SEQUENCE DESCRIPTION: SEQ ID NO:2:

TAGCTTAAGA TACGTATAAT TTTGTTCTAA      30

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: misc_RNA
      (B) LOCATION: 1..20

(xi) SEQUENCE DESCRIPTION: SEQ ID NO:3:

CCTCGACAAC CGCATCCGTT      20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_RNA
        (B) LOCATION: 1..20

(xi) SEQUENCE DESCRIPTION: SEQ ID NO:4:

CCTCGACTAC CGCATCCGTT                                                      20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_RNA
        (B) LOCATION: 1..20

(xi) SEQUENCE DESCRIPTION: SEQ ID NO:5:

CCTCGACCAC TGCATCCGTT                                                      20

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_RNA
        (B) LOCATION: 1..28

(xi) SEQUENCE DESCRIPTION: SEQ ID NO:6:

AGGAATTCAT GACTGAATAT AAACTTGT                                             28

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_RNA
        (B) LOCATION: 1..30

(xi) SEQUENCE DESCRIPTION: SEQ ID NO:7:

ATCGAATTCT ATGCATATTA AAACAAGATT                                           30

(2) INFORMATION FOR SEQ ID NO:8:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: misc_RNA
    (B) LOCATION: 1..18

(xi) SEQUENCE DESCRIPTION: SEQ ID NO:8:

ATTCGTCCAC AAAATGAT                                                 18

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_RNA
        (B) LOCATION: 1..20

(xi) SEQUENCE DESCRIPTION: SEQ ID NO:9:

GGAGCTGGTG GCGTAGGCAA                                               20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_RNA
        (B) LOCATION: 1..20

(xi) SEQUENCE DESCRIPTION: SEQ ID NO:10:

GGAGCTGTTG GCGTAGGCAA                                               20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_RNA
        (B) LOCATION: 1..20

(xi) SEQUENCE DESCRIPTION: SEQ ID NO:11:

GGAGCTGATG GCGTAGGCAA                                               20

(2) INFORMATION FOR SEQ ID NO:12:

(i) SEQUENCE CHARACTERISTICS:
        (A) LENGTH: 20 base pairs
        (B) TYPE: nucleic acid

```
        (C) STRANDEDNESS: single
        (D) TOPOLOGY: linear (ii) MOLECULE TYPE: DNA (genomic)

(ix) FEATURE:
        (A) NAME/KEY: misc_RNA
        (B) LOCATION: 1..20

(xi) SEQUENCE DESCRIPTION: SEQ ID NO:12:

GGAGCTGGTG ACGTAGGCAA                                                 20
```

METHOD FOR DETECTION OF TARGET NUCLEIC ACID BY ANALYSIS OF STOOL

This is a divisional of U.S. application Ser. No. 08/297,265, filed Aug. 26, 1994, U.S. Pat. No. 5,910,407, which is a continuation of Ser. No. 07/861,910, filed Apr. 1, 1992, abandoned.

This invention was made with government support under Grant Number CA35494 by the National Institutes of Health. The government has certain rights in the invention.

BACKGROUND OF THE INVENTION

1. Field of the Invention

This invention relates to a method of detecting a target nucleic acid in stool and reagents usefull therein.

2. Description of Related Art

An increasing body of evidence implicates somatic mutations as causally important in the induction of human cancers. These somatic mutations may accumulate in the genomes of previously normal cells, some of which may then demonstrate the phenotypes associated with malignant growth. Such oncogenic mutations may include a number of different types of alterations in DNA structure, including deletions, translocations and single nucleotide alterations. The latter, also known as point mutations, may frequently intervene in carcinogenesis, in that a variety of mutagenic chemicals induce such mutations. In addition, such mutations may occur spontaneously as a result of mistakes in DNA replication.

Advances in recombinant DNA technology have led to the discovery of normal cellular genes (proto-oncogenes and tumor suppressor genes) which control growth, development, and differentiation. Under certain circumstances, regulation of these genes is altered and they cause normal cells to assume neoplastic growth behavior. There are over 40 known proto-oncogenes and suppressor genes to date, which fall into various categories depending on their functional characteristics. These include, (1) growth factors and growth factor receptors, (2) messengers of intracellular signal transduction pathways, for example, between the cytoplasm and the nucleus, and (3) regulatory proteins influencing gene expression and DNA replication.

Point mutations have been directly implicated in the causation of many human tumors. Some tumors carry oncogenes of the ras gene family, which differ from their normal cellular counterpart proto-oncogenes by the presence of a point mutation at one of a limited number of sites in these genes. Similarly, point mutations in critical regions of tumor suppressor genes, such as p53, are often detected in tumor cells. These mutations represent qualitative changes in the tumor cell genome which distinguish these cells from normal cells and provide a basis for diagnosis of the genetic origin of a tumor under study. Identification of the mutations that have created active oncogenes may provide important diagnostic and prognostic clues for tumor development. For example, a number of mutations have been found to alter the 12th codon of the ras oncogenes, causing replacement of a normally present glycine by any of a number of alternative amino acid residues. Such amino acid substitutions create a potent transforming allele. Thus, the presence of a particular nucleotide substitution may be a strong determinant of the behavior of the tumor cell (e.g., its rate of growth, invasiveness, etc.). As a result, DNA probes of oncogene mutations have promise as diagnostic reagents in clinical oncology.

Among the various types of neoplasms, a number of those which are found in the gastrointestinal tract are associated with oncogenic mutations. This association is particularly significant for colorectal cancer. Colorectal cancer is the third most common malignancy in the world, with 570,000 new cases expected in 1992. In the United States alone, over 60,000 people will die from colorectal cancer in this same year. While patients with advanced disease have a very poor prognosis, colorectal tumors diagnosed at any stage prior to metastasis can usually be cured by surgical or colonoscopic excision. A method to detect surgically resectable tumors could, therefore, considerably reduce deaths from this disease (Winawer, et al., *J. National Cancer Institute,* 83:243, 1991). The only non-invasive test currently available for such a purpose involves testing stool for occult blood. Although stool blood tests may have value in certain circumstances, their utility is controversial, in part because the appearance of hemoglobin in stool is not specific for neoplasia (Ransoboff, et al., *New England Journal of Medicine,* 325:37, 1991; Miller, et al., *Int. J. Cancer,* 46:761, 1990). Although this has stimulated efforts to develop additional, non-invasive tests that could more reliably detect neoplasms of the colon and rectum, such attempts have failed. The present invention addresses this need.

SUMMARY OF THE INVENTION

The present invention arose from the unexpected finding that nucleic acid having a mutant nucleotide sequence associated with gastrointestinal neoplasia is present in detectable levels in stool specimens from patients with gastrointestinal neoplasia.

As a consequence of this discovery, the present invention represents a significant advance over such techniques as tissue biopsy by providing a non-invasive, rapid, and accurate method for detecting mutant nucleotide sequences associated with gastrointestinal neoplasia. Based on this finding, it is now possible to detect various other target nucleic acids associated with other disease states.

DETAILED DESCRIPTION OF THE INVENTION

Figure 1:
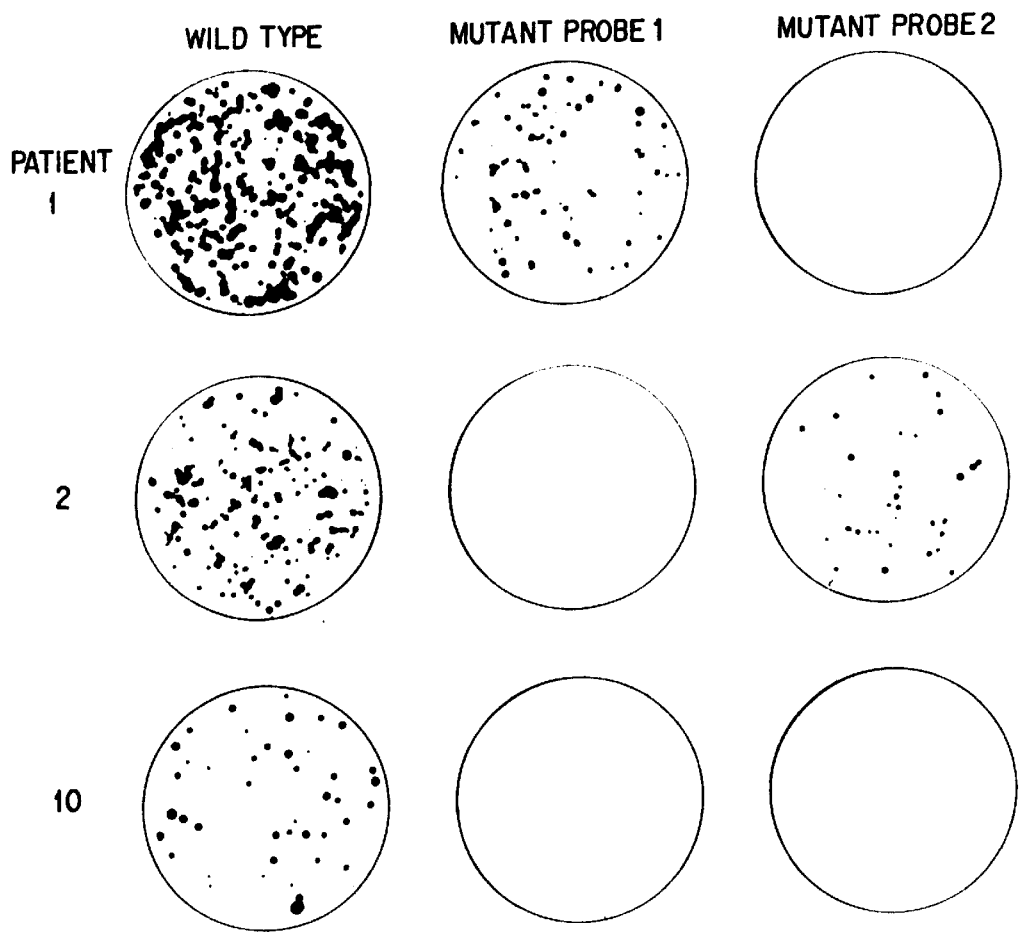
FIG. 1. RAS gene mutations in stool were identified by plaque hybridization. PCR products containing the first coding exon of K-ras were generated from DNA extracted from the stools of patients 1, 2 and 10 (Table 1) and cloned into a bacteriophage vector. The plaque lifts were hybridized to an oligonucleotide specific for wild-type Ras, an oligonucleotide specific for $12^{val}$ (mutant probe 1), and to an oligonucleotide specific for $13^{asp}$ (mutant probe 2). The number of plaques used for hybridization to the mutant specific oligonucleotides was five-fold higher than that used for the wild-type specific oligonucleotide in order to attain a statistically significant number of hybridizing plaques. The ratios of plaques hybridizing to the mutant-specific probe versus the wild-type-specific probe was 0.08:1 and 0.04:1 in patients 1 and 2, respectively.

The present invention relates to a method of detecting a nucleic acid having a mutant nucleotide sequence present in stool, wherein the presence of the altered nucleic acid sequence is associated with neoplasia of the gastrointestinal tract.

In its broadest sense, the present invention allows the detection of any target nucleic acid sequence of diagnostic or therapeutic relevance, where the target nucleic acid sequence is present in stool. Thus, the target nucleotide sequence may be, for example, a mutant nucleotide, a restriction fragment length polymorphism (RFLP), a nucleotide deletion, a nucleotide substitution, or any other mammalian nucleic acid sequence of interest.

In one embodiment, the method of the invention is applicable for detection of mutant nucleotide sequences associated with benign as well as malignant neoplasias. In a preferred embodiment, neoplasia of the gastrointestinal tract, including both the small and large intestine, pancreas, and stomach, is detected, although the method can be used to detect any neoplastic mutant nucleotide sequence, regardless of origin, as long as the sequence is detectably present in stool.

Benign neoplasias of the small intestine include adenomas, leiomyomas, lipomas, and angiomas, whereas large intestine benign neoplasias are primarily adenomatous polyps. The malignant neoplasias of the small intestine include adenocarcinomas, leiomyosarcomas, lymphomas, and carcinoid tumors. In the case of the large intestine and colon, colorectal carcinoma is the most common malignant neoplasia identified.

Numerous nucleic acids having mutant nucleotide sequences that produce an abnormal gene product are known to be associated with various neoplasias. Among the most common mutant nucleotide sequences are oncogenes and tumor suppressor genes, such as mutated in colon cancer (MCC), deleted in colon cancer (DCC), adenomatous polyposis coli (APC), familial adenomatous polyposis coli (FAP) and p53. Of special significance in the present invention is the detection of the K-ras mutant oncogene and the p53 tumor suppressor gene (Vogelstein, *Nature*, 348:681, 1990). Further support for the detection of DCC, MCC, APC, and p53 can be found in U.S. patent applications Ser. Nos. having 07/460,981, filed Jan. 4, 1990; 07/670,611, filed Mar. 13, 1991 issued as U.S. Pat. No. 5,330,892, 07/741,940, filed Aug. 8, 1991; issued as U.S. Pat. No. 5,352,775 and 446,584 filed Dec. 6, 1989, abandoned; respectively, which are incorporated herein by reference.

In order to analyze stool specimens according to the method of the invention, it is necessary to separate the mammalian nucleic acid present in the specimen. There are two primary problems associated with the preparation of mammalian nucleic acid from stool. First, the mammalian nucleic acid must be liberated from the mammalian cells and separated from bacterial cells. This step is further complicated by the fact that It is desirable to avoid releasing nucleic acid from the bacterial cells, since there is such a huge excess of bacterial nucleic acid compared to eukaryotic nucleic acid in the stool specimen. Secondly, once liberated, the mammalian nucleic acid can be protected from the relatively high concentration of nucleases which are present in stool and which could degrade the liberated mammalian nucleic acid and thereby preclude its analysis. In the present invention, it has been found that these stringent criteria can be met by incubating the stool with a specially designed stool lysis buffer which contains a high concentration of buffer of at least about 500 mM, at a pH of at least about 8.0, containing a chelating agent such as EDTA, and a relatively low salt concentration, preferably less than 10 mM.

The stool lysis buffer minimizes nucleic acid degradation by virtue of the pH and chelating properties, lyses eukaryotic cells, but not bacterial cells, and is suitable for further processing to purify and/or concentrate the eukaryotic nucleic acid. After treatment with stool lysis bluffer, the specimen is processed (e.g., by centrifugation) to remove bacteria and other unwanted residues. The non-particulate fraction of the lysate is then incubated with a proteinase (such as 0.5 µg/ml proteinase K) in SDS (1%) to degrade nucleases and other proteins. The nucleic acid in the sample can be further separated by chemical means, such as extraction with phenol/chloroform, ammonium acetate to separate peptides from nucleic acid, and precipitation with ethanol.

In addition, it has been found that stool also contains inhibitors which are preferably removed if the mutant nucleotide sequence present in the stool nucleic acid is to be amplified, such as by polymerase chain reaction (PCR). One of these inhibitors interferes with DNA amplification by Taq polymerase. This inhibitor can be removed by binding the stool nucleic acid to a stationary matrix in the presence of chaotropic salts, such as 6.0M sodium iodide or sodium perchlorate. Surprisingly, it has been found that glass is the preferred matrix for this purpose. Especially preferred commercial versions of glass are Prep-A-Gene™ (Bio-Rad) and Spin-Bind™ (FMC).

The other inhibitor present in stool prevents the binding of nucleic acid to glass. It has been found that this second inhibitor can be removed by binding the inhibitor to a modified ion-exchange resin (e.g., Qiagen) in the presence of high salt concentrations such as at least about 1.0M. Those of skill in the art can envision various ways that the above described process for concentrating and/or purifying mammalian DNA from stool specimens can be modified once it is recognized that mammalian nucleic acid can be selectively obtained from stool specimens. Alternatively, those of skill in the art can ascertain, without undue experimentation, alternative reagents and conditions which are functionally equivalent to those described herein, now that it is known that such methods are practicable on stool specimens. Such modifications and functional equivalents are embraced by the present invention.

Amino acids referred to herein may be identified according to the following three-letter or one-letter abbreviations:

| Amino Acid | Three-Letter Abbreviation | One-Letter Abbreviation |
|---|---|---|
| L-Alanine | Ala | A |
| L-Arginine | Arg | R |
| L-Asparagine | Asn | N |
| L-Aspartic Acid | Asp | D |
| L-Cysteine | Cys | C |
| L-Glutamine | Gln | Q |
| L-Glutamic Acid | Glu | E |
| L-Glycine | Gly | G |
| L-Histidine | His | H |
| L-Isoleucine | Ile | I |
| L-Leucine | Leu | L |
| L-Lysine | Lys | K |
| L-Methionine | Met | M |
| L-Phenylalanine | Phe | F |
| L-Proline | Pro | P |
| L-Serine | Ser | S |

| Amino Acid | Three-Letter Abbreviation | One-Letter Abbreviation |
|---|---|---|
| L-Threonine | Thr | T |
| L-Tryptophan | Trp | W |
| L-Tyrosine | Tyr | Y |
| L-Valine | Val | V |

When it is desired to amplify the mutant nucleotide sequence before detection, this can be accomplished using oligonucleotide(s) which are primers for amplification. These unique oligonucleotide primers are based upon identification of the flanking regions contiguous with the mutant nucleotide sequence. For example, in the case of K-ras, these oligonucleotide primers comprise sequences which are capable of hybridizing with the flanking nucleotide sequence 5'-TCCTTAAGTACTGACTTATATTTGAACA-3', (SEQ ID NO: 1) and/or 5'-TAGCTTAAGATACGTATAATTTTGTTCTAA-3' (SEQ ID NO: 2) and sequences complementary thereto.

The primers which can be used according to the method of the invention embrace oligonucleotides of sufficient length and appropriate sequence so as to provide specific initiation of polymerization of a significant number of nucleic acid molecules containing the target nucleic acid. In this manner, it is possible to selectively amplify the specific target nucleic acid sequence containing the nucleic acid of interest. Specifically, the term "primer" as used herein refers to a sequence comprising two or more deoxyribonucleotides or ribonucleotides, preferably at least eight, which sequence is capable of initiating synthesis of a primer extension product, which is substantially complementary to a target nucleic acid strand. The oligonucleotide primer typically contains 15–22 or more nucleotides, although it may contain fewer nucleotides.

Experimental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition.

Primers used according to the method of the invention are designed to be "substantially" complementary to each strand of mutant nucleotide sequence to be amplified. Substantially complementary means that the primers must be sufficiently complementary to hybridize with their respective strands under conditions which allow the agent for polymerization to function. In other words, the primers should have sufficient complementarily with the flanking sequences to hybridize therewith and permit amplification of the mutant nucleotide sequence. Preferably, the terminus of the primer that is extended has perfectly base paired complementarity with the complementary flanking strand.

Oligonucleotide primers used according to the invention are employed in any amplification process that produces increased quantities of target nucleic acid. Typically, one primer is complementary to the negative (−) strand of the mutant nucleotide sequence and the other is complementary to the positive (+) strand. Annealing the primers to denatured nucleic acid followed by extension with an enzyme, such as the large fragment of DNA Polymerase I (Kenow) or Taq DNA polymerase and nucleotides or ligases, results in newly synthesized + and − strands containing the target nucleic acid. Because these newly synthesized nucleic acids are also templates, repeated cycles of denaturing, primer annealing, and extension results in exponential production of the region (i.e., the target mutant nucleotide sequence) defined by the primer. The product of the amplification reaction is a discrete nucleic acid duplex with termini corresponding to the ends of the specific primers employed. Those of skill in the art will know of other amplification methodologies which can also be utilized to increase the copy number of target nucleic acid.

The oligonucleotide primers for use in the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters*, 22:1859–1862, 1981). One method for synthesizing oligonucleotides on a modified solid support is described in U.S. Pat. No. 4,458,066. One method of amplification which can be used according to this invention is the polymerase chain reaction (PCR) described in U.S. Pat. Nos. 4,683,202 and 4,683,195.

Any stool specimen nucleic acid, in purified or nonpurified form, can be utilized as the starting nucleic acid or acids, provided it contains, or is suspected of containing, the specific nucleic acid sequence containing the target nucleic acid. Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The mutant nucleotide sequence to be amplified, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

Where the target mutant nucleotide sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means; the word "denaturing" includes all such means. One physical method of separating nucleic acid strands involves -heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (*CSH-Quantitative*

*Biology,* 43:63, 1978) and techniques for using RecA are reviewed in C. Radding (*Ann. Rev. Genetics,* 16:405–437, 1982).

If the nucleic acid containing the target nucleic acid to be amplified is single stranded, its complement is synthesized by adding one or two oligonucleotide primers. If a single primer is utilized, a primer extension product is synthesized in the presence of primer, an agent for polymerization, and the four nucleoside triphosphates described below. The product will be complementary to the single-stranded nucleic acid and will hybridize with a single-stranded nucleic acid to form a duplex of unequal length strands that may then be separated into single strands to produce two single separated complementary strands. Alternatively, two primers may be added to the single-stranded nucleic acid and the reaction carried out as described.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7–9, most preferably about 8. Preferably, a molar excess. (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

In some amplification embodiments, the substrates, for example, the deoxyribonucleotide triphosphates dATP, dCTP, dGTP, and dTTP, are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, *E. coli* DNA polymerase 1, Taq polymerase, Klenow fragment of *E. coli* DNA polymerase 1, T4 DNA polymerase, other available DNA polymerases, polymerase muteins, reverse transcriptase, ligase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each mutant nucleotide strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above. In any event, the method of the invention is not to be limited to the embodiments of amplification which are described herein.

The newly synthesized mutant nucleotide strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The above process is repeated on the single-stranded molecules. Additional agent for polymerization, nucleosides, and primers may be added, if necessary, for the reaction to proceed under the conditions prescribed above. Again, the synthesis will be initiated at one end of each of the oligonucleotide primers and will proceed along the single strands of the template to produce additional nucleic acid. After this step, half of the extension product will consist of the specific nucleic acid sequence bounded by the two primers.

The steps of denaturing and extension product synthesis can be repeated as often as needed to amplify the target mutant nucleotide sequence to the extent necessary for detection. The amount of the mutant nucleotide sequence produced will accumulate in an exponential fashion.

The amplified product may be detected by analyzing it by Southern blots without using radioactive probes. In such a process, for example, a small sample of DNA containing a very low level of mutant nucleotide sequence is amplified, and analyzed via a Southern blotting technique. The use of non-radioactive probes or labels is facilitated by the high level of the amplified signal.

Nucleic acids having a mutation detected in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology,* 3:1008–1012, 1985), allele-specific oligonucleotide (ASO) probe analysis (Conner, et al., *Proc. Natl. Acad. Sci. USA,* 80:278, 1983), oligonucleotide ligation assays (OLAs) (Landegren, et al., *Science,* 241:1077, 1988), and the like. Molecular techniques for DNA analysis have been reviewed (Landegren, et al., *Science,* 242:229–237, 1988). Thus, in a preferred embodiment where the mutant nucleotide sequence to be detected is K-ras, a hybridization probe is utilized which is capable of hybridizing with mutant nucleotide sequences comprising 5'-CCTCGACAACCGCATCCGTT-3' (SEQ ID NO: 6), 5'-CCTCGACTACCGCATCCGTT-3', or 5'-CCTCGACCACTGCATCCGTT-3', and sequences complementary thereto.

In an embodiment of the invention, purified nucleic acid fragments containing intervening sequences or oligonucleotide sequences of 10–50 base pairs are radioactively labelled. The labelled preparations are used to probe nucleic acid from stool by the Southern hybridization technique. Nucleotide fragments from stool, before or after amplification, are separated into fragments of different molecular masses by gel electrophoresis and transferred to filters which bind nucleic acid. After exposure to the labelled probe, which will hybridize to nucleotide fragments containing target nucleic acid sequences, binding of the radioactive probe to target nucleic acid fragments is identified by autoradiography (see *Genetic Engineering,* 1, ed. Robert Williamson, Academic Press, (1981), 72–81). Alternatively, nucleic acid from stool can be bound directly to filters to which the radioactive probe selectively binds nucleic acids having the sequence of interest specific sequences and the degree of binding is quantitated by directly counting the radioactive emissions.

Where the target nucleic acid is not amplified, detection using an appropriate hybridization probe may be performed directly on the separated mammalian nucleic acid. In those instances where the target nucleic acid is amplified, detection with the appropriate hybridization probe would be performed after amplification.

The probes of the present invention can be used for examining the distribution of the specific fragments detected, as well as the quantitative (relative) degree of binding of the probe for determining the occurrence of specific strongly binding (hybridizing) sequences, thus indicating the likelihood for an individual to be at low risk or high risk for neoplastic disease, such as colorectal carcinoma.

For the most part, the probe will be labelled with an atom or inorganic radical, most commonly using radionuclides, but also perhaps heavy metals. Conveniently, a radioactive label may be employed. Radioactive labels include $^{32}P$, $^{125}I$, $^{3}H$, $^{14}C$, or the like. Any radioactive label may be employed which provides for an adequate signal and has sufficient half-life. Other labels include ligands, which can serve as a specific binding pair member for a labelled ligand, and the like. A wide variety of labels have been employed in immunoassays which can readily be employed in the present assay. The choice of the label will be governed by the effect of the label on the rate of hybridization and binding of the probe to mutant nucleotide sequence. It will be necessary that the label provide sufficient sensitivity to detect the amount of mutant nucleotide sequence available for hybridization. Other considerations will be ease of synthesis of the probe, readily available instrumentation, ability to automate, convenience, and the like.

The manner in which the label is bound to the probe will vary depending upon the nature of the label. For a radioactive label, a wide variety of techniques can be employed. Commonly employed is nick translation with an a $^{32}P$-dNTP or terminal phosphate hydrolysis with alkaline phosphatase followed by labeling with radioactive $^{32}P$ employing $^{32}P$-NTP and T4 polynucleotide kinase. Alternatively, nucleotides can be synthesized where one or more of the elements present are replaced with a radioactive isotope, e.g., hydrogen with tritium. If desired, complementary labelled strands can be used as probes to enhance the concentration of hybridized label.

Where other radionuclide labels are involved, various linking groups can be employed. A terminal hydroxyl can be esterified, with inorganic acids, e.g., $^{32}P$ phosphate, or $^{14}C$ organic acids, or else esterified to provide linking groups to the label. Alternatively, intermediate bases may be substituted with activatable linking groups which can then be linked to a label.

Enzymes of interest as reporter groups will primarily be hydrolases, particularly esterases and glycosidases, or oxidoreductases, particularly peroxidases. Fluorescent compounds include fluorescein and its derivatives, rhodamine and its derivatives, dansyl, umbelliferone, and so forth. Chemiluminescers include luciferin, and 2,3-dihydrophthalazinediones (e.g., luminol).

The probe can be employed for hybridizing to a nucleotide sequence affixed to a water insoluble porous support. Depending upon the source of the nucleic acid, the manner in which the nucleic acid is affixed to the support may vary. Those of ordinary skill in the art know, or can easily ascertain, different supports which can be used in the method of the invention.

The nucleic acid from a stool specimen is spotted or spread onto a filter to provide a plurality of individual portions. The filter is an inert porous solid support, e.g., nitrocellulose. Any mammalian cells present in stool are treated to liberate their nucleic acid. The lysing and denaturation of nucleic acid, as well as the subsequent washings, can be achieved with an appropriate solution for a sufficient time to lyse the cells and denature the nucleic acid. For lysing, chemical lysing will conveniently be employed, as described previously for the stool lysis buffer. Other denaturation agents include elevated temperatures, organic reagents, e.g., alcohols, amides, amines, ureas, phenols and sulfoxides or certain inorganic ions, e.g., thiocyanate and perchlorate.

After denaturation, the filter is washed in an aqueous buffered solution, such as Tris, generally at a pH of about 6 to 8, usually 7. One or more washings may be involved, conveniently using the same procedure as employed for the lysing and denaturation. After the lysing, denaturing, and washes have been accomplished, the nucleic acid spotted filter is dried at an elevated temperature, generally from about 50° C. to 70° C. Under this procedure, the nucleic acid is fixed in position and can be assayed with the probe when convenient.

Pre-hybridization may be accomplished by incubating the filter at a mildly elevated temperature for a sufficient time with the hybridization solution without the probe to thoroughly wet the filter. Various hybridization solutions may be employed, comprising from about 20% to 60% volume, preferably 30%, of an inert polar organic solvent. A common hybridization solution employs about 50% formamide, about 0.5 to 1M sodium chloride, about 0.05 to 0.1M sodium citrate, about 0.05 to 0.2% sodium dodecylsulfate, and minor amounts of EDTA, ficoll (about 300–500 kD), polyvinylpyrrolidone, (about 250–500 kD) and serum albumin. Also included in the hybridization solution will generally be from about 0.5 to 5 mg/ml of sonicated denatured DNA, e.g., calf thymus or salmon sperm; and optionally from about 0.5 to 2% wt/vol glycine. Other additives may also be included, such as dextran sulfate of from about 100 to 1,000 kD and in an amount of from about 8 to 15 weight percent of the hybridization solution.

The particular hybridization technique is not essential to the invention. Other hybridization techniques are described by Gall and Pardue, *Proc. Natl. Acad. Sci.* 63:378, 1969; and John, et al., *Nature,* 223:582, 1969. As improvements are made in hybridization techniques they can readily be applied in the method of the invention.

The amount of labelled probe which is present in the hybridization solution will vary widely, depending upon the nature of the label, the amount of the labelled probe which can reasonably bind to the filter, and the stringency of the hybridization. Generally, substantial excess over stoichiometric concentrations of the probe will be employed to enhance the rate of binding of the probe to the fixed target nucleic acid.

Various degrees of stringency of hybridization may be employed. The more severe the conditions, the greater the complementarily that is required for hybridization between the probe and the single stranded target nucleic acid sequence for duplex formation. Severity can be controlled by temperature, probe concentration, probe length, ionic strength, time, and the like. Conveniently, the stringency of hybridization is varied by changing the polarity of the reactant solution by manipulating the concentration of formamide in the range of 20% to 50%. Temperatures employed will normally be in the range of about 20° C. to 80° C., usually 30° C. to 75° C. (see, generally, *Current Protocols in Molecular Biology,* Ausubel, ed., Wiley & Sons, 1989).

After the filter has been contacted with a hybridization solution at a moderate temperature for a period of time sufficient to allow hybridization to occur, the filter is then introduced into a second solution having analogous concentrations of sodium chloride, sodium citrate and sodium dodecylsulfate as provided in the hybridization solution. The time for which the filter is maintained in the second solution may vary from five minutes to three hours or more. The second solution determines the stringency, dissolving cross duplexes and short complementary sequences. After rinsing the filter at room temperature with dilute sodium citrate-sodium chloride solution, the filter may now be assayed for the presence of duplexes in accordance with the nature of the label. Where the label is radioactive, the filter is dried and exposed to X-ray film.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method.

For example, one of the container means may comprise a hybridization probe which is or can be detectably labelled. A second container may comprise a stool lysis buffer. The kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radionuclide label.

The above disclosure generally describes the present invention. A more complete understanding can be obtained by reference to the following specific examples which are provided herein for purposes of illustration only and are not intended to limit the scope of the invention.

EXAMPLE 1

Detection of Neoplastic DNA from Stool Specimens

An initial study was performed to analyze tumors from twenty-four patients for the presence of K-ras gene mutations at codons 12 or 13. These cases comprised a consecutive series of clinical patients from whom stool samples could be obtained prior to bowel preparation for colonoscopy or surgery and who were later found to have either a malignant, colorectal tumor (carcinoma) or a benign tumor (adenoma) greater than 1 cm in diameter. Adenomas of this size are clinically the most important, as they are much more likely to progress to malignancy than smaller tumors.

The first exon of the K-ras gene was amplified from DNA purified from cryostat sections of these tumors (Fearon, et al., *Nature,* 318:377, 1985) using the polymerase chain reaction (PCR). For PCR, the sense primer was 5'-AGGAATTCATGACTGAATATAAACTTGT-3' (SEQ ID NO: 6) and the antisense primer was 5'-ATCGAATTCTATGCATATTAAAACAAGATT-3' (SEQ ID NO: 7). These primers included EcoRI sites at their 5' ends to facilitate cloning. Each cycle of PCR consisted of a denaturing step at 95° C. for 30 s, followed by annealing at 55° C. for 30 s and extension at 70° C. for 45 s. For each PCR, 500 ng template DNA and 5 units Taq polymerase were used in a 50 µl reaction containing 1.5 and mM dNTP's, 16.6 mM ammonium sulfate, 67 mM Tris, pH 8.8, 8.67 mM $MgCl_2$, 10 mM β-mercaptoethanol, and 10% dimethylsulfoxide. In this specific example, 35 cycles were performed for tumor DNA and 45 cycles for stool DNA.

The PCR products were cloned en masse, and pooled to identify mutations. PCR products were purified by phenol-chloroform extraction and ethanol precipitation. They were cleaved with EcoRI, repurified, and approximately 50 ng of DNA was ligated to lambda Zap II vector arms (Stratagene) and packaged according to the manufacturer's directions. XLI Blue cells (Stratagene) were infected with bacteriophage and double-stranded plasmids were obtained using a helper phage (Nigro, et al., *Nature,* 342:705, 1989). A minimum of 100 clones was pooled for sequencing using the primer 5'-ATTCGTCCACAAAATGAT-3' (SEQ ID NO: 8). In this study, 9 of the twenty-four tumors (37%) were found to contain mutations of this exon. Three different mutations were identified (codon 12:gly→val or asp; codon 13:gly→asp). These data were consistent with previous studies in similar tumors which showed that approximately 50% contained Ras gene mutations, with 84% of the mutations confined to codons 12 or 13 of K-ras (Vogelstein, et al., *N. Engl. J. Med.,* 319:525, 1988).

Next, stools from the first two of the nine patients were analyzed. Several methods to purify DNA were evaluated, and the most reproducible procedure subsequently used. In this procedure, approximately 100 mg of stool frozen at −80° C. was diluted with 300 µl of lysis buffer (500 mM Tris, 50 mM EDTA, 10 mM NaCl, pH 9.0) vortexed, and particulates and most bacteria removed by centrifugation (12,000 g, 2 min, 30 s). DNA in the supernatant was purified by SDS-proteinase K digestion, phenol chloroform extraction, and ethanol precipitation (Goelz, et al., *Biochem Biophys Res. Commun.,* 13:118, 1985). The DNA from stool was then further purified by binding to glass beads (Vogelstein and Gillespie, *Proc. Natl. Acad. Sci. USA,* 76:615, 1978) using a Prepagene matrix (BioRad). Five microliters of matrix was used to purify the DNA from 100 mg of stool, following the conditions specified by the manufacturer. Typically, 0.5 to 5.0 µg of DNA was obtained.

The first exon of the K-ras gene was then PCR-amplified from this DNA in the same fashion as described above for the DNA from the tumors. Because it was initially expected that mutant Ras genes would represent only a small fraction of the total Ras genes in stool (if present at all), a very sensitive technique for analysis was used for K-ras which involved cloning in bacteriophage. This technique had previously been shown to allow identification of a small fraction of mutant p53 genes in the urine of patients with advanced bladder cancers and to reveal the existence of even one mutant gene among several thousand normal genes (Sidransky, et al., *Science,* 252:706, 1991).

SL1 cells infected with bacteriophage containing PCR products were plated on L-agar at a density of 100–2,000 plaques per plate, transferred to nylon membranes, and hybridized with oligonucleotides specific for wild-type or mutant K-ras genes. Hybridization was performed for one hour at 50° C. in buffer H (0.9M sodium chloride, 0.005M, EDTA, 0.05 M sodium phosphate, pH 7.0, 1% sodium dodecyl sulfate (SDS), 0.5% non-fat dried milk, 10% formamide and 6% polyethylene glycol 6000) containing $10^7$ dpm/ml probe. Washes were performed at 63° C. in 450 mM sodium chloride, 18 mM sodium citrate, 1 mm Tris, pH7.2, 0.1% SDS for 15 mins. Films were exposed for 1–8 hours at −80° C. with intensifying screens. The oligonucleotides used for hybridization were 5'-GGAGCTGGTGGCGTAGGCAA-3' (SEQ ID NO: 9) for wild-type (wt) Ras, 5'-GGAGCTGTTGGCGTAGGCAA-3' (SEQ ID NO: 10) for the $12^{val}$ mutant, 5'-GGAGCTGATGGCGTAGGCM-3' (SEQ ID NO: 11) for the $12^{asp}$ mutant, and 5'-GGAGCTGGTGACGTAGGCM-3' (SEQ ID NO: 12) for the $13^{asp}$ mutant. Oligonucleotides were labelled to a specific activity of approximately $10^8$ dpm/μg using T4 polynucleotide kinase.

Figure 2:
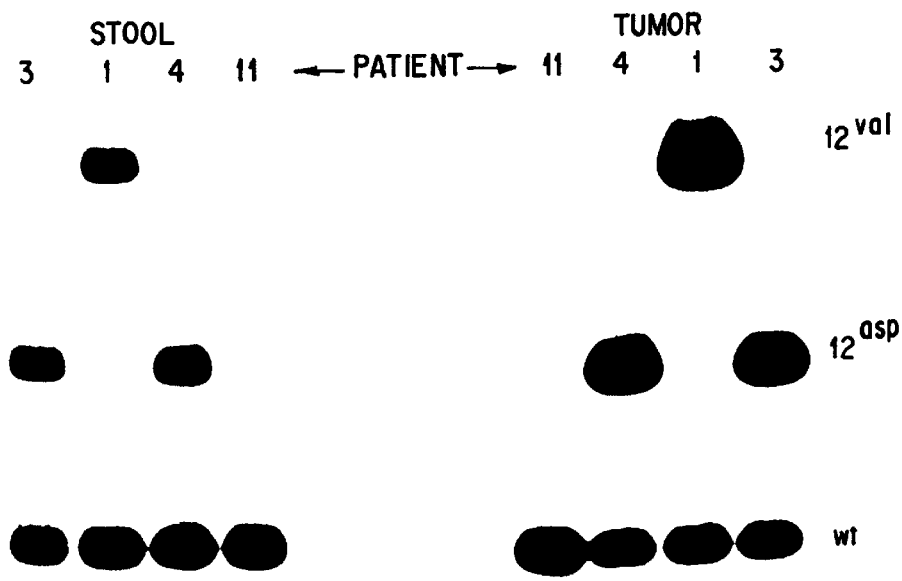
FIG. 2. RAS gene mutations were detected using a Southern blot assay of PCR amplified products. PCR products containing the first coding exon of K-ras were generated from DNA extracted from stools and tumors of patents 1, 3, 4, and 11. PCR products were subjected to electrophoresis through a 2% agarose gel and transferred to nylon filters. The blots were hybridized to oligonucleotide probes specific for wild-type RAS (lower panel), the $12^{asp}$ mutation (middle panel), or the $12^{val}$ mutation (top panel). The stool and tumor DNA samples from patients 3 and 4 contained a $12^{asp}$ mutation, while those from patient 1 contained a $12^{val}$ mutation. Neither the stool DNA nor the tumor DNA of patient 11 contained either of these mutations.

Analysis of these findings surprisingly showed that both patients contained mutant Ras genes in the DNA purified from their stool samples. The mutant genes detected in the stool were the same as those detected in the tumors ($12^{val}$ in the stool and tumor of patient 1; $13^{asp}$ in the stool of patient 2, FIG. 1). A control stool sample from a patient without a Ras gene mutation in his tumor contained no mutations -at either of these positions (FIG. 1, patient 10).

sequence, in this case the various K-ras genes, crude PCR products were simply subjected to electrophoresis through an agarose gel and transferred to nylon filters by the method of Southern. These blots were then incubated with radiolabelled oligonucleotides recognizing wild-type or mutant K-ras genes. Examples of the results are shown in FIG. 2 for paired tumor and stool samples. The $12^{val}$ mutation found in patient 1 was easily observed in her stool using the Southern blot assay (FIG. 2, top panel). The oligonucleotides specific for the $12^{asp}$ mutant provided a negative control (FIG. 2, middle panel). The wild-type specific oligonucleotide hybridized to DNA from both tumor and stool, as expected (FIG. 2, lower panel). Similarly, Southern blot analysis revealed that the tumors and stool of the DNA from patients 3 and 4 both contained the $12^{asp}$ mutation, while neither hybridized to the $12^{val}$-specific oligonucleotide (FIG. 2). The ratio of mutant to wild-type hybridization in the stool samples was 5–10 fold lower than that in the tumors, consistent with the plaque hybridization assays.

The stools from all nine patients were analyzed by Southern blot analysis and mutations were detected in eight of them (TABLE I). Mutations originating in benign tumors (patients 2 and 9) as well as malignant tumors were detectable in the stool. Tumors as small as 1.3 cm³ gave rise to detectable mutant genes in the stool (patient 2). Moreover, the locations within the bowel did not appear critical because even very proximal tumors (patient 9, cecum; patient 7, ascending colon) gave positive results.

TABLE I

PATIENTS STUDIED FOR STOOL RAS GENE MUTATIONS

| PATIENT | AGE/SEX | TUMOR LOCATION | TUMOR TYPE/STAGE[1] | TUMOR SIZE | TUMOR MUTATION[2] | MUTANT RAS GENE IN STOOL[3] |
|---|---|---|---|---|---|---|
| 1 | 52/F | Rectum | Carcinoma/C | 5.8 × 6.5 × 2.7 cm | $12^{val}$ | + |
| 2 | 63/M | Sigmold Colon | Adenoma | 1.5 × 1.5 × 0.6 cm | $13^{asp}$ | + |
| 3 | 51/F | Rectum | Carcinoma/C | 2.8 × 2.0 × 0.4 cm | $12^{asp}$ | + |
| 4 | 61/M | Rectum | Carcinoma/C | 2.5 × 4.7 × 1.8 cm | $12^{asp}$ | + |
| 5 | 70/M | Rectum | Carcinoma/A | 1.0 × 0.9 × 0.4 cm | $13^{asp}$ | − |
| 6 | 71/M | Rectum | Carcinoma/B | 5.9 × 6.4 × 1.7 cm | $12^{asp}$ | + |
| 7 | 51/F | Ascend Colon | Carcinoma/B | 4.3 × 3.4 × 1.4 cm | $12^{asp}$ | + |
| 8 | 69/M | Sigmold Colon | Carcinoma/B | 4.8 × 3.0 × 1.2 cm | $13^{asp}$ | + |
| 9 | 67/M | Cecum | Adenoma | 6.0 × 4.0 cm[5] | $12^{asp}$ | + |
| 10 | 61/M | Splenic Flex | Carcinoma/C | 1.2 × 6.5 cm[5] | None | − |
| 11 | 34/M | Sigmold Colon | Carcinoma/B | 7 × 3 × 2 cm | None | − |
| 12 | 63/M | Sigmold Colon | Carcinoma/C | 2.1 × 3.1 × 0.4 cm | None | − |
| 13 | 42/F | NA[4] | NA | — | NA | − |
| 14 | 53/F | NA | NA | — | NA | − |
| 15 | 63/F | NA | NA | — | NA | − |

[1]Carcinomas were classified according to Duke (13): A = Confined to muscularls propria; B = Extension through muscular propria; but confined to colon; C = Metastatic to regional lymph nodes.
[2]Determined by sequence analysis of codons 12 or 13 of K-Ras (as described in text).
[3]As assessed by the plaque hybridization or Southern blot assay using three mutant specific oligomers ($12^{val}$, $12^{asp}$, and $13^{asp}$) as proves (see text).
[4]Patients 13, 14, and 15 had no colorectal neoplasms found at colonoscopy (NA = Not Applicable).
[5]Only measurements of the external surfaces of these tumors were available.

The fraction of phage plaques hybridizing to the mutant-specific oligonucleotide in patients 1 and 2 was quite high, representing 8% and 4%, respectively, of the phage hybridizing to the oligonucleotide specific for the wild-type K-ras gene. These unexpected findings indicated that a less sensitive, but simpler, assay that can be used to identify mutant genes in stool samples.

In order to explore the possibility that a simpler and more rapid technique could be used to detect a specific target As controls, six stool samples were examined, three from patients with no colorectal neoplasia and three from patients with colorectal tumors that did not contain K-ras mutations at codons 12 or 13. In all six cases, strong hybridization to the wild-type-specific oligonucleotides, but not to the oligonucleotides specific for $12^{val}$, $12^{asp}$, or $13^{asp}$ mutations, was observed (TABLE I, examples in FIGS. 1 and 2).

The results of these experiments provide an embodiment wherein successful detection of neoplasia was accomplished and provides a practical basis for a new approach for detecting the presence of neoplasias, such as colorectal tumors, in a non-invasive fashion. The approach would have utility in monitoring patient populations on different diets or treatments designed to minimize the incidence of neoplasia. It also could be used in screening asymptomatic patients, especially those at risk by virtue of inherited or environmental factors, for the presence of neoplasia. The current results indicate that a significant fraction of early colorectal cancers and dangerous pre-malignant lesions can be identified through this strategy. Additionally, these findings indicate that other mutant nucleotide sequences, besides K-ras, which are associated or indicative of gastrointestinal neoplasias would also be detectable in stool specimens. Such sequences include, for example, the genes for DCC, MCC, FAP, and APC where p53 can be found.

The above disclosure generally describes the present invention. A more complete understanding can be obtained by reference to the following specific examples which are provided herein for purposes of illustration only and are not intended to limit the scope of the invention.

What is claimed is:

1. A method for separating mammalian nucleic acid from a stool specimen comprising:
   (a) removing particulate matter from a stool specimen in stool lysis buffer to produce a non-particulate fraction; and
   (b) separating the nucleic acid from the non-particulate fraction.

2. The method of claim 1, wherein the non-particulate fraction is treated to degrade nucleases.

3. The method of claim 2, wherein the treated non-particulate fraction is extracted to concentrate the nucleic acid.

4. The method of claim 2, further comprising at least one of the steps of binding the nucleic acid to glass in the presence of a chaotropic salt or binding the nucleic acid to a modified ion-exchange matrix.

5. The method of claim 1, wherein the stool lysis buffer has a pH from about 8.0 to about 9.0, a chelating agent at a concentration from about 10 mM to about 200 mM, and a salt concentration from about 1 mM to about 20 mM.

6. The method of claim 5, wherein the chelating agent is EDTA.

7. The method of claim 5, wherein the salt is NaCl.

8. The method of claim 1, wherein the particulate matter is removed by centrifugation.

9. The method of claim 2, wherein the nucleases are degraded with proteinase K.

10. The method of claim 3, wherein the non-particulate fraction is extracted with phenol-chloroform and precipitated with ethanol.

11. A stool lysis buffer comprising:
    at least 500 mM buffer;
    a chelating agent at a concentration from about 10 mM to about 20 mM; and
    a salt at a concentration from about 1 mM to about 20 mM;
    at a pH of greater than 8.0 to about 9.0.

12. The buffer of claim 11, wherein the chelating agent is EDTA.

13. The buffer of claim 11, wherein the salt is NaCl.

14. The buffer of claim 11, further comprising Tris at a concentration from about 500 mM to about 1 M.

15. The method of claim 1 wherein the stool lysis buffer lyses mammalian cells selectively relative to bacterial cells present in the stool specimen.

16. The method of claim 1 wherein the stool specimen is of an asymptomatic patient.

17. The method of claim 1 wherein the stool specimen is of a person at risk of cancer by virtue of inherited or environmental factors.

18. The method of claim 1 wherein the stool sample is collected from a person receiving treatments to reduce the incidence of neoplasia.

19. The method of claim 1 wherein the stool sample is collected from a person on a diet to reduce the incidence of neoplasia.

20. The method of claim 1 wherein the nucleic acid is tested for the presence of a mutation in a gene selected from the group consisting of K-ras, DCC, MCC, APC, and p53.

21. The method of claim 1 wherein the nucleic acid is subsequently amplified.

22. The method of claim 1 wherein the nucleic acid is subsequently amplified by polymerase chain reaction.

23. The method of claim 1 wherein the stool lysis buffer comprises at least 500 mm buffer.

24. The method of claim 1 wherein the stool lysis buffer comprises Tris at a concentration of from about 500 mM to 1 M.

25. The method of claim 5 wherein the stool lysis buffer comprises at least 500 mM buffer.

26. The method of claim 5 wherein the stool lysis buffer comprises Tris at a connection of from about 500 mM to 1 M.

* * * * *

UNITED STATES PATENT AND TRADEMARK OFFICE
CERTIFICATE OF CORRECTION

PATENT NO.     : 6,177,251 B1
DATED          : January 23, 2001
INVENTOR(S)    : Bert Vogelstein et al.

It is certified that error appears in the above-identified patent and that said Letters Patent is hereby corrected as shown below:

Column 15,
Line 26, sequence listing, after "(xi) SEQUENCE DESCRIPTION: SEQ ID NO:2", "TAGCTTAAGA TACGTATAAT TTTGTTCTAA" has been replaced with -- AATCTTGTTT TAATATGCAT AGAATTCGAT --.
Line 38, sequence listing, after "(xi) SEQUENCE DESCRIPTION: SEQ ID NO:3", "CCTCGACAAC CGCATCCGTT" has been replaced with -- TTGCCTACGC CAACAGCTCC --.

Column 17,
Line 12, after "(xi) SEQUENCE DESCRIPTION: SEQ ID NO:4", "CCTCGACTAC CGCATCCGTT" has been replaced with -- TTGCCTACGC CATCAGCTCC --.
Line 24, after "(xi) SEQUENCE DESCRIPTION: SEQ ID NO:5:", "CCTCGACCAC TGCATCCGTT" has been replaced with -- TTGCCTACGT CACCAGCTCC --.

Signed and Sealed this

Tenth Day of June, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,177,251 B1 Page 1 of 1
DATED : January 23, 2001
INVENTOR(S) : Bert Vogelstein et al.

It is certified that error appears in the above-identified patent and that said Letters Patent is hereby corrected as shown below:

Column 5,
Line 19, "5'-TCCTTAAGTACTGACTTATATTTGAACA-3'" has been replaced with -- 3'-TCCTTAAGTACTGACTTATATTTGAACA-5' --.
Line 21, "5'-TAGCTTAAGATACGTATAATTTTGTTCTAA-3'" has been replaced with -- 3'-TAGCTTAAGATACGTATAATTTTGTTCTAA-5' --.

Column 8,
Lines 60-62, "5'-CCTCGACAACCGCATCCGTT-3' (SEQ ID NO:66), 5'-CCTCGACTACCGCATCCGTT-3', or 5'-CCTCGACCACTGCATCCGTT-3'", has been replaced with -- 3'-CCTCGACAACCGCATCCGTT-5' (SEQ ID NO:3), 3'-CCTCGACTACCGCATCCGTT-5' (SEQ ID NO:4), or 3'-CCTCGACCACTGCATCCGTT-5' (SEQ ID NO:5) --.

Column 15,
Line 14, in the sequence listing, after "(xi) SEQUENCE DESCRIPTION: SEQ ID NO:1:", "TCCTTAAGTA CTGACTTATA TTTGAACA" has been replaced with -- ACAAGTTTAT ATTCAGTCAT GAATTCCT --.

Signed and Sealed this

Twenty-third Day of December, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,177,251 B1
DATED : January 23, 2001
INVENTOR(S) : Bert Vogelstein et al.

It is certified that error appears in the above-identified patent and that said Letters Patent is hereby corrected as shown below:

Column 21,
Line 50, please replace "20 mM" with -- 200 mM --

Signed and Sealed this

Twenty-second Day of March, 2005

JON W. DUDAS
*Director of the United States Patent and Trademark Office*